United States Patent [19]
Butler et al.

[11] Patent Number: 5,373,750
[45] Date of Patent: Dec. 20, 1994

[54] CERAMIC COMPOSITE MATERIAL MECHANICAL BEHAVIOUR SIMULATION

[75] Inventors: Edwin Butler, Warwick; Paul A. Doleman, Derby, both of England

[73] Assignee: Rolls-Royce plc, London, United Kingdom

[21] Appl. No.: 937,676

[22] Filed: Sep. 1, 1992

[30] Foreign Application Priority Data

Oct. 29, 1991 [GB] United Kingdom ............... 9122873

[51] Int. Cl.$^5$ ............................................. G01N 19/00
[52] U.S. Cl. ..................................... 73/866.4; 73/804
[58] Field of Search ................... 73/804, 788, 866.4

[56] References Cited

U.S. PATENT DOCUMENTS 3,974,124  8/1976  Pelham, Sr. .

5,014,558  5/1991  Yano et al. .......................... 73/804

FOREIGN PATENT DOCUMENTS 0323541  7/1989  European Pat. Off. .
2221914  2/1990  United Kingdom .

*Primary Examiner*—Robert Raevis
*Attorney, Agent, or Firm*—Oliff & Berridge

[57] ABSTRACT

The mechanical behavior of a given component formed from reinforcing ceramic fibers enclosed in a ceramic matrix is determined by subjecting a dummy component to mechanical testing. The dummy component is formed from low modulus organic resin fibers enclosed in a matrix of an organic resin having a correspondingly low modulus. The organic resin fibers have the same configuration and fiber architecture as those of the ceramic fibers.

8 Claims, No Drawings

CERAMIC COMPOSITE MATERIAL MECHANICAL BEHAVIOUR SIMULATION

This invention relates to a method of simulating the mechanical behaviour of ceramic composite materials. It additionally relates to a non-ceramic composite material for use in such a method of simulation.

Ceramic composite materials are becoming increasingly attractive for use in the manufacture of components which are required to operate in high temperature environments. Gas turbine engine turbine components are a typical example of those which could be usefully made from ceramic composite materials.

One important feature of ceramic composite materials, particularly those which are required to function in mechanically arduous conditions, is their reinforcing fibre architecture. Fibre architecture is the particular arrangement of fibres in a component which provides that component with the desired strength characteristics.

The conventional procedure for determining particular fibre architectures is to use theoretical measures to arrive at the architecture and then carry out experimental work to confirm the suitability of that architecture. The drawback with this approach is that ceramic fibres are costly and their fabrication processes are complicated and time consuming. Thus whereas it may be theoretically possible to arrive at a large number of different fibre architectures for a given application, it is not practical to produce all of those architectures and mechanically test them.

It is an object of the present invention to provide a method of mechanically testing ceramic composite material fibre architectures which does not actually involve manufacturing those ceramic composite materials.

It is a further object of the present invention to provide a composite material for use in such mechanical testing.

According to the present invention, a method of determining the mechanical behaviour of a given component formed from a given composite material comprising reinforcing ceramic fibres enclosed in a ceramic matrix comprises the steps of forming a dummy component having the same configuration and fibre architecture as said given component from low modulus of elasticity organic resin fibres enclosed in a correspondingly low modulus of organic resin matrix and subsequently subjecting that dummy component to mechanical testing.

According to a further aspect of the present invention, a composite material comprises reinforcing low modulus organic resin fibres enclosed in a correspondingly low modulus organic resin matrix.

In the manufacture of composite material comprising reinforcing fibres enclosed in an organic resin matrix, the normal practice to ensure that the low modulus of the matrix material is matched by fibres which are of high modulus. However we have found that if the fibres are also of low modulus, then in certain respects the resultant composite material acts in the same way as a composite material comprising ceramic fibres enclosed in a ceramic matrix. Specifically, the resultant composite material has mechanical behaviour properties which are very similar to those of such a ceramic/ceramic composite material.

We have found that this similarity in mechanical behaviour properties can be utilised in assessing the relative merits of different fibre architectures ceramic/ceramic composite materials. This is done by manufacturing a composite material component comprising low modulus organic resin fibres in a correspondingly low modulus organic resin binder. The manufactured component is a dummy which is of the same configuration and has the same fibre architecture as the proposed ceramic/ceramic component. The component itself may be in the form of an actual device or part of a device or it may be in the form of a test-piece.

If the dummy component is then subjected to mechanical behaviour testing, we have found in comparative tests that it behaves, mechanically, in the same way as a structurally similar component comprising ceramic fibres enclosed in a ceramic matrix. This means that the use of such dummy components is useful in investigating various possible fibre architectures for ceramic/ceramic composites. Consequently the dummy components, since they are formed from low cost materials are easy to manufacture, prove a cheap and effective way of assessing the mechanical performance of ceramic/ceramic composite components. Several potentially useful fibre architectures can then be assessed for their mechanical performance without the difficulty and expense of using ceramic materials. When the apparently best fibre architectures have been determined by mechanical testing of the dummy components, then a small number of ceramic/ceramic composite material components may be manufactured for confirmatory tests.

One organic resin fibre/matrix system which we have found to be effective in simulating the mechanical behaviour characteristics of ceramic composite materials comprises polyester fibres enclosed in a polyester resin matrix. The specific resin matrix used was Spectra "VBR Polyester Resin" hardened using Pergan "Hardener for Polyester". The fibre used was Enka "Diolen Type 174S High Tenacity Polyester Filament Yarn".

The resin and hardener were mixed in a ratio of 50:1 by weight and stirred vigorously until all of the hardener had dissolved. The mixture was then stood in an ultrasonic bath for two minutes to disperse any air bubbles.

Sufficient of the resultant resin/hardener mixture was then poured into a mould to coat the bottom of the mould whereupon a layer of the polyester fibres was pressed into the matrix. Further resin/hardener mixture was then poured on to the fibres and a further layer of fibres in the desired fibre architecture were added. This process was repeated until the fibre layers had been built up to the necessary level.

The fibre layers were then subjected to a load of 50KN for a period of four hours until the resin had set. After reducing the pressure on the mould, it was subjected to the following cure cycle:
24 hours at room temperature
2 hours at 180° C.

Finally the component was allowed to cool to room temperature and was removed from the mould.

A further organic resin fibre/matrix system which we have found to be effective in simulating the mechanical behaviour characteristics of ceramic/ceramic composite materials comprises polyester fibres enclosed in an epoxy resin matrix. The specific resin matrix used was Ciba-Geigy "Araldite MY750" resin, hardened using Ciba-Geigy "Araldite hardner HT972". The fibre used was Enka "Diolen Type 174S High Tenacity Polyester Filament Yarn".

The resin and hardener were mixed in a ratio of 5:1 by weight and then heated at 85° C. and stirred until all of the hardener had dissolved. The resin and hardener mixture was then used to impregnate the polyester fibres in a mould in the same manner as described in the previous example. The resin/hardener impregnated fibres were then pressed in the mould with a load of 50KN for a period of 24 hours.

After reducing the mould pressure, the moulded component was subjected to the following cure cycle:

15 hours at 60° C.
2 hours at 80° C.
½ hour at 100° C.
1 hour at 140° C.
2 hours at 180° C.

Finally the component was allowed to cool to room temperature and was removed from the mould.

Components manufactured in accordance with the examples described above were found in tests to exhibit mechanical behaviour properties similar to those of ceramic/ceramic composite materials such as silicon carbide fibres in a silicon carbide matrix. The tests employed were those which are commonly used in assessing the mechanical properties of composite materials, for instance those intended to determine tensile and flexural strength. Subsequent tests using the same fibre architectures as in the dummy components but using ceramic/ceramic composite materials demonstrated that the dummy components were effective in predicting the mechanical properties of the ceramic/ceramic composite materials.

In order to carry out the mechanical testing of the dummy components, they were made in the form of test pieces of the necessary standard shapes. It will be appreciated, however, that the dummy components could be in the form of actual structures or sub-elements of those structures depending upon the type of mechanical testing desired to be carried out.

Although the present invention has been described with reference to dummy components formed from particular resin systems, it will be appreciated that other suitable resin systems may be used if so desired. The important feature of such systems however is that the fibres and the matrix must have correspondingly low modulii.

We claim:

1. A method of determining the mechanical behaviour of a given component formed from a given composite material comprising reinforcing ceramic fibres enclosed in a ceramic matrix, comprising the steps of forming a dummy component having the same configuration and fibre architecture as said given component from low modulus of elasticity organic resin fibres enclosed in a correspondingly low modulus of elasticity organic resin matrix and subsequently subjecting that dummy component to mechanical testing.

2. A method of determining the mechanical behaviour of a given component as claimed in claim 1 wherein said dummy component is in the form of a test-piece appropriately configured for a specific type of mechanical testing.

3. A method of mechanically testing a ceramic composite material having a fiber architecture, comprising:
   forming low modulus of elasticity organic resin fibers enclosed in a corresponding low modulus of elasticity organic resin matrix into a dummy component having a configuration according to a configuration of said ceramic composite material and having a fiber architecture according to a fiber architecture of said ceramic composite material; and
   mechanically testing said dummy component.

4. The method of claim 3, wherein said organic resin fibers are polyester fibers.

5. The method of claim 3, wherein said organic resin matrix is a polyester resin matrix.

6. The method of claim 3, wherein said organic resin fibers enclosed in an organic resin matrix comprise polyester fibers enclosed in an epoxy resin matrix.

7. The process of claim 3, wherein said forming said organic resin fibers enclosed in an organic resin matrix comprises:
   coating the bottom of a mold with a resin and hardener mixture; and
   pressing a layer of polyester fibers into said mixture until fiber layers have formed said dummy component.

8. The method of claim 7, wherein resin and hardener are mixed in a ratio of 5 to 1 by weight and heated at about 85° C. to form said resin and hardener mixture.

* * * * *